United States Patent [19]

Rahlwes et al.

[11] Patent Number: 4,654,452

[45] Date of Patent: Mar. 31, 1987

[54] ISOMERIZATION PROCESS

[75] Inventors: William C. Rahlwes; Ralph G. Carrasco, Jr., both of Old Ocean, Tex.

[73] Assignee: Phillips Petroleum Company, Bartlesville, Okla.

[21] Appl. No.: 450,492

[22] Filed: Dec. 16, 1982

[51] Int. Cl.$^4$ ............................................... C07C 5/22
[52] U.S. Cl. .................................. 585/253; 585/350; 585/365
[58] Field of Search ................ 585/251, 253, 350, 365

[56] References Cited

U.S. PATENT DOCUMENTS

| | | | |
|---|---|---|---|
| 2,953,606 | 9/1960 | Dean et al. | 585/253 |
| 3,150,195 | 9/1964 | Findlay | 585/253 |
| 3,233,001 | 2/1966 | Merryfield et al. | 585/253 |
| 3,248,438 | 4/1966 | Kron | 585/253 |
| 3,249,642 | 5/1966 | Walaby et al. | 585/253 |
| 3,250,819 | 5/1966 | Cabbage | 585/253 |
| 3,260,762 | 7/1966 | Cabbage | 585/253 |
| 3,264,361 | 8/1966 | Schellenberg | 585/253 |
| 3,311,667 | 3/1967 | Cabbage | 585/253 |

FOREIGN PATENT DOCUMENTS 606798  3/1948  United Kingdom ................ 585/365

Primary Examiner—William R. Dixon, Jr.
Assistant Examiner—Cynthia A. Prezlock
Attorney, Agent, or Firm—C. F. Steininger

[57] ABSTRACT

A hexanes stream, conventionally produced in petroleum refining, comprising normal hexane, isohexanes, methylcyclopentane, and cyclohexane is isomerized to produce primarily cyclohexane and to recover normal hexane by first fractionating the hexanes stream in a first fractionation step in a manner and under conditions to produce a normal hexane-isohexane rich overhead stream and a methylcyclopentane-cyclohexane rich bottoms stream, the bottoms stream is isomerized in the presence of an isomerization catalyst and under conditions sufficient to maximize the conversion of methylcyclopentane to cyclohexane, the overhead from the first fractionation step and the effluent from the isomerization step is then fractionated in at least one stage of a second fractionation step in a manner and under conditions to produce separate streams, comprising isohexanes, normal hexane, cyclohexane, and unreacted methylcyclopentane and the methylcyclopentane is recycled to the isomerization step and/or the first fractionation step. Since an original hexane stream usually contains benzene, it is preferred that the original hexane stream be hydrogenated to convert the benzene to cyclohexane prior to passing the feed to the first fractionation step.

10 Claims, 1 Drawing Figure

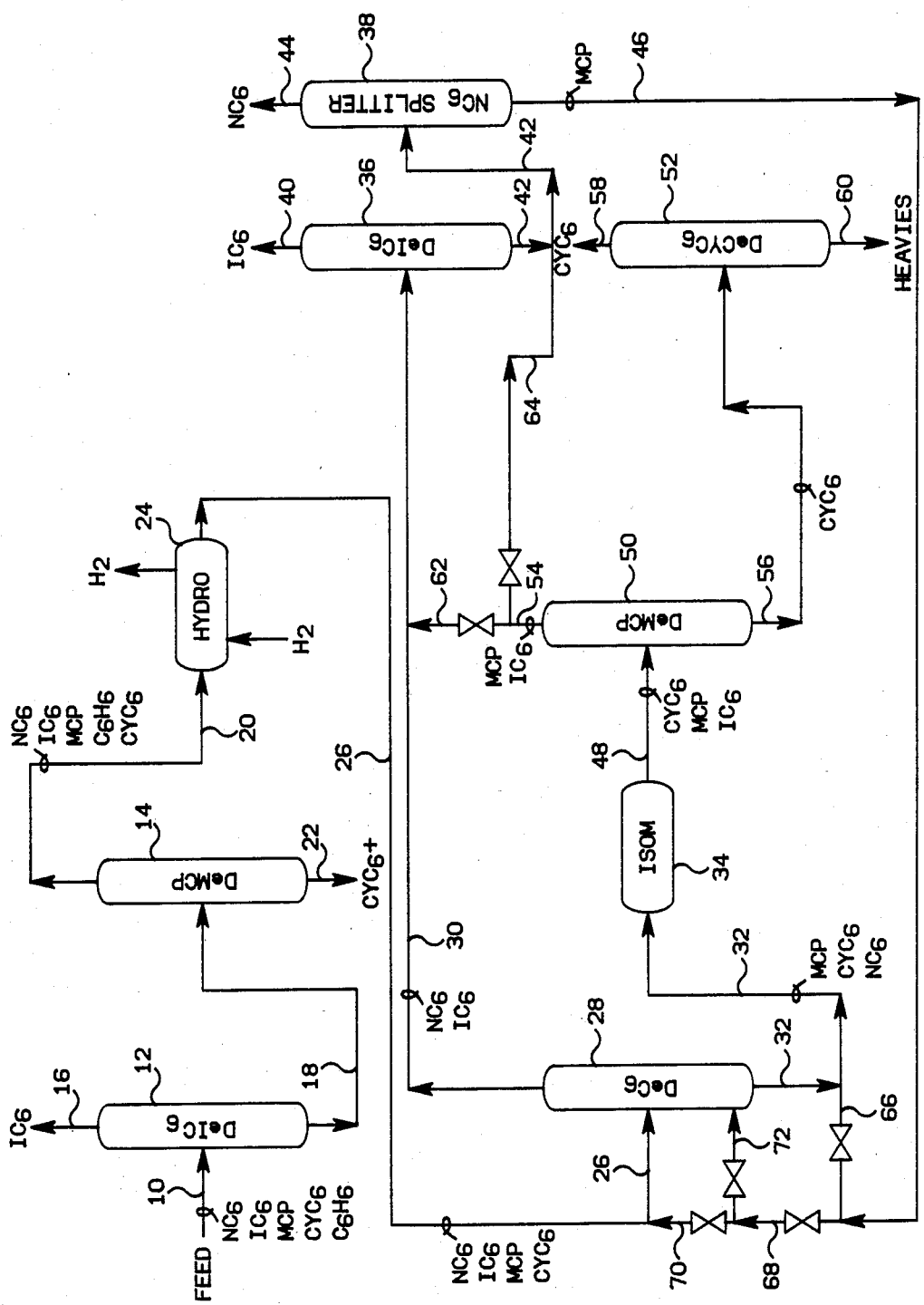

ISOMERIZATION PROCESS

The present invention relates to an improved process for the isomerization of $C_6$ hydrocarbons. More specifically, the present invention relates to an improved process for the isomerization of $C_6$ hydrocarbon streams to maximize the conversion to cyclohexane and the recovery of normal hexane.

BACKGROUND OF THE INVENTION

Refinery streams normally subjected to isomerization contain varying amounts of normal hexane, isohexanes, methylcyclopentane, cyclohexane and benzene. In the isomerization of such feedstreams, the feedstream is first treated with hydrogen to hydrogenate benzene to cyclohexane. Thereafter, the resulting product is isomerized, primarily to convert methylcyclopentane to cyclohexane. Consequently, one of the problems involved in such isomerization processes is maximizing cyclohexane production, since this material is a valuable chemical intermediary. During the course of such isomerization, normal hexane present in the feed to the isomerization is converted to isohexane. However, although isohexanes are useful as motor fuel blending stocks, the normal hexane, which is useful as a solvent, is substantially more valuable than isohexanes. Consequently, another problem involved is the recovery of normal hexane during the processing of the feedstream and, to the extent possible, suppressing the production of isohexanes from normal hexane. As in any other catalytic process, it is highly desirable to reduce the load or throughput to the isomerization step, since this will normally lengthen the life of the catalyst, improve conversion to desired products, and conserve energy. Since such isomerization systems include a large number of fractionation stages in order to separately recover normal hexane, isohexanes and cyclohexane, as products, such a system is highly energy intensive. Consequently, it is yet another problem to reduce the energy requirements of the system.

SUMMARY OF THE INVENTION

It is therefore an object of the present invention to provide an improved isomerization system which overcomes the above mentioned and other problems of the prior art. Another object of the present invention is to provide an improved isomerization system which maximizes the conversion of methylcyclopentane to cyclohexane. A further object of the present invention is to provide an improved isomerization system which maximizes the recovery of normal hexane from a $C_6$ hydrocarbon feedstream. Another and further object of the present invention is to provide an improved isomerization system which reduces fractionation for the recovery of products. A still further object of the present invention is to provide an isomerization system which reduces the energy requirements. Yet another object of the present invention is to provide an improved isomerization system which reduces the volume of feed to the isomerization step. A further object of the present invention is to provide an improved isomerization system which extends catalyst life and reduces losses from the isomerization step. These and other objects of the present invention will be apparent from the following description.

In accordance with the present invention, a hexanes stream, comprising normal hexane, isohexanes, methylcyclopentane and cyclohexane, is first fractionated to produce a normal hexane-isohexanes rich overhead and a methylcyclopentane-cyclohexane rich bottoms stream. The bottoms stream is then isomerized to maximize the conversion of methylcyclopentane to cyclohexane, the overhead from the first fractionating step and the effluent from the isomerization step are then fractionated in a second fractionation step to produce separate streams of isohexanes, normal hexane, cyclohexane and unreacted methylcyclopentane and the unreacted methylcyclopentane is recycled to either or both of the isomerization step and the first fractionation step. The original $C_6$ feedstream is preferably hydrogenated to convert any benzene present to cyclohexane prior to the isomerization step.

BRIEF DESCRIPTION OF THE DRAWING

The single FIGURE of the drawings shows a flow diagram of an isomerization system in accordance with the present invention.

DESCRIPTION OF THE PREFERRED EMBODIMENTS

The present invention will be best understood and described in conjunction with the single FIGURE of drawings.

A typical $C_6$ or hexanes original feedstream to an isomerization system, in the refining art, generally comprises normal hexane, isohexanes, methylcyclopentane, cyclohexane, and benzene. This original feedstream is introduced to the system through line 10. In order to reduce the load on the hereinafter mentioned isomerization step and thus save energy, extend the catalyst life, reduce losses of catalysts, and, in general, increase the conversion to the desired products, it is desirable to remove isohexanes and cyclohexane which are ultimate products of the system to the extent possible prior to isomerization. Consequently, the original feedstream is fed to a preliminary fractionation step which includes a first stage 12 and a second stage 14. In the first stage 12, referred to as a deisohexanizer, the feedstream is separated into an overhead stream rich in isohexanes, discharged through line 16, and a bottoms stream rich in normal hexane, methylcyclopentane, cycylohexane and benzene, which is discharged through line 18. The bottoms stream then passes to the second stage fractionator, referred to as a demethylcyclopentanizer, wherein the stream is separated to an overhead stream, rich in normal hexane, isohexanes, methylcyclopentane and cyclohexane, which passes through line 20 and a bottoms stream, rich in cyclohexane, discharged through line 22. The overhead stream is then charged to a hydrogenation reactor 24 where it is contacted with a suitable hydrogenation catalyst in the presence of hydrogen in a manner and under conditions to convert benzene to cyclohexane. Benzene hydrogenation zone 24 can be any known hydrogenation type process for converting benzene to cyclohexane under conditions for such conversion. Generally, the temperature in a hydrogenation zone will range from about 350° F. to about 450° F. at a pressure ranging from about 400 psig to about 500 psig. Suitable catalysts that can be employed include conventional nickel catalysts and platinum catalysts. Any suitable type of contacting technique, for example, fixed bed, moving bed, etc. can be used for effecting hydrogenation of the benzene present in the feed.

The effluent from the hydrogenation zone 24 is passed through line 26. This effluent stream generally contains normal hexane, isohexanes, methylcyclopentane and cyclohexane. In conventional practice, the stream from line 26 is fed to at least one isomerization unit. However, in accordance with the present invention, again to utilize the isomerization step more effectively, to obtain greater conversion of the desired products, save energy and at the same time permit recovery of greater volumes of normal hexane, the feed through line 26 is passed to a first fractionation step 28. In fractionator 28, the feedstream is fractionated in a manner and under conditions to obtain an overhead stream rich in normal hexane and containing lighter materials and some isohexanes which is then passed through line 30 and a bottoms stream which is discharged through line 32 and which is rich in methylcyclopentane and cyclohexane and in the remaining normal hexane.

In accordance with the present invention, only the bottoms stream rather than the total feedstream is isomerized in isomerization unit 34. Isomerization unit 34 may be any conventional isomerization unit or a plurality of units in parallel, etc. The isomerization may be carried out in the presence of a suitable conventional catalyst, for example, an aluminum chloride complex, and in a fixed bed, moving bed, or other suitable contacting technique for effecting contact between the hydrocarbon feed and the catalyst. Other catalysts that can be used include conventional platinum or alumina type catalysts. Generally, reaction conditions include a temperature in the range of about 115° F. to about 125° F. and a pressure of about 140 psig to about 160 psig. Contact time or residence time of the hydrocarbon in contact with the catalyst can range from about 30 minutes to about 90 minutes. In isomerization unit 34, methylcyclopentane is converted to cyclohexane and any normal hexane, which may be present, is converted to isohexanes. However, as previously indicated, it is more economically attractive to convert as little normal hexane to isohexane as possible. Accordingly, the normal hexane separated in fractionator 28 is not passed through an isomerization reactor as is conventional practice. This has the distinct advantage that the feed flow to isomerization unit 34 is reduced to about one-third of that normally fed to an isomerization unit utilizing an original feed such as that referred to herein. This reduction in the feed to the isomerization unit increases the conversion of methylcyclopentane to cyclohexane, since a longer residence time results, and reduces the losses of catalysts such as aluminum chloride and hydrogen chloride from the system. Obviously also, the recovery of normal hexane from the system is increased since anywhere from 30 to 70 percent of the normal hexane normally fed to an isomerization unit will be converted to isohexanes in the isomerization unit.

The normal hexane rich overhead stream passing through line 30 is therefore passed directly to fractionation rather than an isomerization unit. Specifically, this overhead stream is passed to a second fractionation step including a first stage 36 and a second stage 38 operated in a manner and under conditions to recover a substantially pure isohexane stream and a substantially pure normal hexane stream. Specifically, the feed to fractional unit 36 is separated into an isohexane rich overhead stream, discharged through line 40, and a normal hexane rich bottoms stream, discharged through line 42. The bottoms stream from line 42 is fed to the second stage 38 of the second fractionation step which separates a substantially pure normal hexane stream, discharged through line 44, as an overhead and a bottoms stream, rich in unreacted methylcyclopentane, which is discharged through line 46.

The effluent from isomerization unit 34, and discharged through line 48, predominates in cyclohexane, unreacted methylcyclopentane and isohexanes from the original feed and from conversion of normal hexane present in the isomerizer. This stream is then fed to a third fractionation step for the recovery of isohexanes, normal hexane, methlcyclopentane, and cyclohexane as separate streams. This accomplished by passing same to a third fractionation step which includes a first stage 50 and a second stage 52. In the first stage 50, the hydrocarbon stream is fractionated to obtain an overhead stream comprising primarily methylcyclopentane, isohexanes, and any remaining normal hexane which is discharged through line 54. The bottoms fraction is rich in cyclohexane and contains heavier hydrocarbons and is discharged through line 56. The bottoms fraction then passes to the second stage 52 of the third fractionation step to recover a substantially pure cyclohexane stream discharged as an overhead through line 58 and a fraction heavier than cyclohexane discharged through line 60.

The overhead stream from line 54 may be either passed through line 62 to the second fractionation step or preferably through line 64, which bypasses the first stage of the second fractionation step. If this overhead stream is passed through line 62, it is combined with the overhead stream passing through line 30 and fed to the first stage of the second fractionation step and ultimately to the second stage 38 of the second fractionation step for the recovery of isohexanes and normal hexane and the separation of unreacted methylcyclopentane. However, substantial savings can be effected by bypassing the first stage 36 of the second fractionation step and adding the overhead stream from line 64 to the bottoms fraction of the first stage 36 and then passing the combined stream to the second stage of the second fractionation step for further separation. The latter is made possible by the fact that the overhead stream from fractionator 50 contains only small amounts of isohexanes, as was previously pointed out, since most of the normal hexane is removed from the feedstream and does not pass through the isomerization unit 34. There is little conversion of normal hexane to isohexane and hence small amounts of isohexane in the product from the isomerization unit. Thus, unnecessary fractionation is eliminated. The low severity or degree of fractionation requires less heat, usually supplied by steam, for heating fractionation units and there are ultimate significant savings in energy.

Unreacted methylcyclopentane passing through line 46 may be recycled either to the isomerization unit 34 or the first fractionation step, carried out in fractionator 28. Accordingly, this recycled stream is passed through line 66 to isomerization unit 34 or through line 68 to fractionator 28. The latter procedure is more desirable to the extent that any normal hexane and isohexanes present in the recycled stream may be preliminarily removed thus again reducing the load on isomerization unit 34. Also the recycled stream passing through line 68 may be combined with the feed to fractionator 28 through line 70 and/or passed through line 72 to the bottom of fractionation 28. The latter procedure is more desirable since the recycle stream is a heavy stream and, if introduced adjacent the bottom of fractionator 28, acts as a stripping medium for the feed introduced to fractionator 28 through line 26.

The following calculated example is representative of a typical operation of the inventive process as described above in connection with the FIGURE. The table below sets forth the flow in barrels/hour of the major hydrocarbon components through significant flow lines and items of equipment. The numbers at the head of the columns refer to the flow lines of the figure.

TABLE

| Bbl/hr | 26 | 32 | 66 | 32 + 66 | 48 | 54 | 30 | 40 | 42 | 42 + 34 | 44 | 56 |
|---|---|---|---|---|---|---|---|---|---|---|---|---|
| IC$_6$ | 57.6 | .2 | 0 | .2 | 4.3 | 4.3 | 57.4 | 41.0 | 16.4 | 20.7 | 20.7 | 0 |
| NC$_6$ | 68.4 | 5.5 | 2.7 | 8.2 | 4.1 | 4.1 | 63.0 | 4.7 | 58.3 | 62.4 | 59.7 | 0 |
| MCP | 40.7 | 32.2 | 9.0 | 41.2 | 12.4 | 11.9 | 8.5 | .1 | 8.4 | 20.3 | 11.3 | .5 |
| CyC$_{6+}$ | 16.0 | 16.0 | .3 | 16.3 | 44.1 | .3 | 0 | 0 | 0 | .3 | 0 | 44.1 |
| Totals | 182.7 | 53.9 | 12.0 | 55.9 | 64.9 | 20.6 | 128.9 | 45.8 | 83.1 | 103.7 | 91.7 | 44.6 |

While specific reactions, conditions, items of equipment, flow schemes, and the like have been referred to in the prior description, it is to be understood that these specific recitals are for purposes of illustration only and to set forth the best mode in accordance with the present invention and are not to be considered limiting.

That which is claimed is:

1. A method for isomerizing a hexanes stream, comprising normal hexane, isohexanes, methylcyclopentane and cyclohexane, comprising:
   (a) fractionating said hexanes stream in a first fractionation step in a manner and under conditions to produce a normal hexane-isohexane rich stream and a methylcyclopentane-cyclohexane rich stream;
   (b) isomerizing said methylcyclopentane-cyclohexane rich stream from said first fractionation step in at least one isomerization step, in the presence of an isomerization catalyst and under conditions to maximize the conversion of methylcyclopentane to cyclohexane;
   (c) fractionating the effluent from said isomerization step in at least one stage of a third fractionation step in a manner and under conditions to produce a cyclohexane rich stream and an isohexane-methylcyclopentane rich stream;
   (d) fractionating said normal hexane-isohexane rich stream from said first fractionation step and said isohexane-methylcyclopentane rich stream from said third fractionation step in at least one stage of a second fractionation step in a manner and under conditions to produce a normal hexane rich stream, an isohexane rich stream and an unreacted methylcyclopentane stream; and
   (e) recycling the thus produced unreacted methylcyclopentane stream to said first fractionation step.

2. A method in accordance with claim 1 wherein the thus recycled methylcyclopentane stream is recycled to the first fractionation step at a point lower than the point of introduction of the hexanes stream.

3. A method in accordance with claim 1 wherein the thus recycled methylcyclopentane stream is combined with the hexanes stream to the first fractionation step.

4. A method in accordance with claim 1 wherein at least part of the isohexane-methylcyclopentane rich stream from the third fractionation step and the normal hexane-isohexane rich stream from the first fractionation step are fractionated in a first stage of the second fractionation step in a manner and under conditions to produce the isohexane rich stream and a normal hexane-methylcyclopentane rich stream, the remainder, if any, of said isohexane-methylcyclopentane rich stream from the third fractionation step and said normal hexane-methylcyclopentane rich stream from said first stage of said second fractionation step are fractionated in a second stage of said second fractionation step in a manner and under conditions to produce the normal hexane rich stream and the unreacted methylcyclopentane stream.

5. A method in accordance with claim 4 wherein all of the isohexane-methylcyclopentane rich stream from the third fractionation step and the normal hexane-isohexane rich stream from the first fractionation step are fractionated in the first stage of the second fractionation step.

6. A method in accordance with claim 1 wherein the normal hexane-isohexane rich stream from the first fractionation step is fractionated in a first stage of the second fractionation step in a manner and under conditions to produce the isohexane rich stream and a normal hexane-methylcyclopentane rich stream and the isohexane-methylcyclopentane rich stream from the third fractionation step and said normal hexane-methylcyclopentane rich stream from said first stage of said third fractionation step are fractionated in a second stage of said second fractionation step in a manner and under conditions to produce the normal hexane rich stream and the unreacted methylcyclopentane stream.

7. A method in accordance with claim 1 wherein the effluent from the isomerization step is fractionated in a first stage of the third fractionation step in a manner and under conditions to produce the isohexane-methylcyclopentane rich stream and a cyclohexane-heavier hydrocarbon rich stream and said cyclohexane-heavier hydrocarbon rich stream from said first stage of said second fractionation step is fractionated in a second stage of said third fractionation step in a manner and under conditions to produce the cyclohexane rich stream and a heavier hydrocarbon rich stream.

8. A method in accordance with claim 1 wherein the hexanes stream is obtained from an original feedstream additionally containing benzene by hydrogenating said original feedstream in the presence of a hydrogenation catalyst and hydrogen and under conditions sufficient to convert said benzene to cyclohexane.

9. A method in accordance with claim 8 wherein the original feedstream is preliminarily fractionated in at least one stage of a preliminary fractionation step in a manner and under conditions to produce an isohexanes rich stream, a cyclohexane rich stream and a benzene-normal hexane-isohexane-methylcyclopentane-cyclohexane rich stream and said benzene-normal hexane-isohexane-methylcyclopentane-cyclohexane rich stream is thus hydrogenated.

10. A method in accordance with claim 9 wherein the preliminary fractionation step comprises a first stage and a second stage, the original feedstream is fractionated in said first stage of said preliminary fractionation step in a manner and under conditions to produce the isohexane rich stream and a heavier hydrocarbon stream, said heavier hydrocarbon stream is fractionated in said second stage of said preliminary fractionation step in a manner and under conditions to produce the cyclohexane rich stream and a lighter hydrocarbon stream and said lighter hydrocarbon stream from said second stage of said preliminary fractionation step is thus hydrogenated.

* * * * *